United States Patent [19]

Nishimura et al.

[11] Patent Number: 4,650,868
[45] Date of Patent: Mar. 17, 1987

[54] 7-DEAZAPURINE DERIVATIVES USEFUL AS ANTITUMOR AGENTS

[75] Inventors: Susumu Nishimura, Chiba; Hiroaki Nomura, Osaka; Hiroshi Akimoto, Hyogo, all of Japan

[73] Assignee: Takeda Chemical Industries, Ltd., Osaka, Japan

[21] Appl. No.: 729,202

[22] Filed: May 1, 1985

[30] Foreign Application Priority Data

May 2, 1984 [JP] Japan ................... 59-89049

[51] Int. Cl.$^4$ .......................................... C07D 471/02
[52] U.S. Cl. .................................. 544/280; 544/117; 544/229
[58] Field of Search ................ 544/280, 117, 276, 229

[56] References Cited

U.S. PATENT DOCUMENTS

| 4,435,569 | 3/1984 | Nishimura et al. | 544/280 |
| 4,435,570 | 3/1984 | Nishimura et al. | 544/280 |
| 4,571,423 | 2/1986 | Nomura et al. | 544/280 |
| 4,595,530 | 6/1986 | Nishimura et al. | 544/280 |

FOREIGN PATENT DOCUMENTS

| 0075881 | 4/1983 | European Pat. Off. . |
| 0079447 | 5/1983 | European Pat. Off. . |
| 0119591 | 9/1984 | European Pat. Off. . |
| 58-85889 | 5/1983 | Japan . |

Primary Examiner—Donald G. Daus
Assistant Examiner—Stephen N. Kapner
Attorney, Agent, or Firm—Wegner & Bretschneider

[57] ABSTRACT

7-Deazapurine derivatives of the formula:

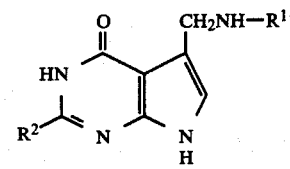

wherein $R^1$ is phenyl which has, at the ortho position and/or para position as substituents, at least one group represented by the formula $-O-R^3$, $-S-R^4$ or

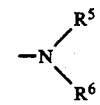

(wherein $R^3$, $R^4$, $R^5$ and $R^6$ are the same or different and each is hydrogen or an alkyl or phenyl group which may be substituted, whereby $R^5$ and $R^6$, together with the adjacent nitrogen atom, may form a cyclic amino group which may be substituted, and $R^3$, $R^4$, $R^5$ and $R^6$ each may represent a protective group), and may have a group or groups with a molecular weight of up to about 200 as a substituent at any position other than those having the said substituents introduced; $R^2$ is an amino group which may be protected, or its salt, have a potent antitumor activity, and hence the compounds are useful as an antitumor agent.

11 Claims, No Drawings

7-DEAZAPURINE DERIVATIVES USEFUL AS ANTITUMOR AGENTS

The present invention relates to 7-deazapurine derivatives which are useful as an antitumor agent.

Natural modified bases (for example, Q base, PreQ$_1$ base) are widely distributed in the animal, vegetable and microbial kingdoms as the constituent base for the first letter of the anticodons for specific tRNA (tRNA$^{Tyr}$, tRNA$^{His}$, tRNA$^{Asp}$ and tRNA$^{Asn}$). These Q bases are thought to exert directly important biological effects over the functions of tRNA converting the recognition of the genetic information from mRNA and protein synthesis.

With the recent advance of fundamental research in the biochemical field, on the other hand, the structures of tRNAs and the role they play in vital phenomena have been elucidated little by little. One of the most important results is the fundamental research on the differences in tRNA of Q bases between a cancer cell and a normal cell. Thus, a cancer cell differs from a normal cell in that the uptake of Q bases into tRNA precursors is incomplete and that there invariably exist Q-deficient tRNAs. Also, the presence of tRNA-guanine transglucosidase in cancer cells has been confirmed as has been the case with normal cells, and it has been observed that when a Q base is supplied from an external source, such a Q-base deficient tRNA takes the Q base into the predetermined position (the first letter of the anticodon) and thereby returns to the normal tRNA, and that generally the uptake of Q bases is not observed in normal cells but is specific to cancer cells [Nishimura S., "Taisha" (Metabolism), vol. 17, Special Issue "Gan (cancer) 80", p. 127–]36 (1980); G. Nass, Recent Results in Cancer Research 84/Modified Nucleosides and Cancer, Springer-Verlag, Berlin Heidelberg-New York (1983)].

Heretofore, extensive research has been carried out for the purpose of obtaining drugs effective for the therapy of cancers, but it is strongly demanded to develop a drug functioning on the basis of a new mechanism of action which exhibits improved efficacy and enhanced selectivity toward cancer cells.

The present inventors, after synthesis of various derivatives of Q bases and intensive research into effects of these on cancer cells, found compounds which exhibit improved antitumor activities based on the novel mechanism of action. The finding was followed by further research, which led to completion of this invention.

The present invention is concerned with 7-deazapurine derivatives of the formula:

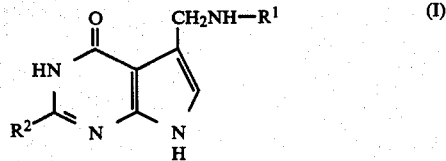

wherein R$^1$ is phenyl which has, at the ortho position and/or para position as substituent(s), at least one group represented by the formula —O—R$^3$, —S—R$^4$ or

(wherein R$^3$, R$^4$, R$^5$ and R$^6$ are the same or different and each is hydrogen or an alkyl or phenyl group which may be substituted, wherein R$^5$ and R$^6$, together with the adjacent nitrogen atom, may form a cyclic amino group, and R$^3$, R$^4$, R$^5$ and R$^6$ each may represent a protective group) and may have one, two or three groups with a molecular weight of up to about 200 as a substituent at any position other than those having the said substituents; R$^2$ is an amino group which may be protected or its salt.

Referring to the above formula, the alkyl or phenyl group which may be substituted as represented by R$^3$, R$^4$, R$^5$ and R$^6$ includes preferably one of those having a molecular weight of not more than about 400.

The said alkyl group is preferably one of those having 1 to 24 carbon atoms, and their examples include methyl, ethyl, propyl, isopropyl, butyl, isobutyl, sec-butyl, tert-butyl, pentyl, isopentyl, hexyl, isohexyl, heptyl, octyl, nonyl, decyl, undecyl, dodecyl, tetradecyl, hexadecyl, octadecyl, nonadecyl, eicosanyl, heneicosanyl, decosanyl, tricosanyl, tetracosanyl, 1,2-dimethylpropyl, 1-ethylpropyl, 1,2,2-trimethylpropyl, 1-propylbutyl, 2-ethylhexyl, etc.

R$^5$ and R$^6$, together with the adjacent nitrogen atom, may form a ring. Such a ring includes for example about 5-or 6-membered cyclic amino groups, which may have a second cyclic hetero atom (e.g., N, O) in addition to the above nitrogen atom. Their examples include, for example, pyrrolidinyl, pyrrolinyl, pyrrolyl, imidazolidinyl, imidazolyl, pyrazolidinyl, pyrazolinyl, pyrazolyl, morpholino, dihydropyridyl, piperidino, N-methylpiperazinyl, N-ethylpiperazinyl, etc.

The group which may be substituted on the said alkyl or phenyl group or the cyclic amino group to be formed by R$^5$ and R$^6$ together with the adjacent nitrogen atom, includes, for example, alkyl group of 1 to 4 carbon atoms (e.g., methyl, ethyl, propyl, isopropyl, sec-butyl, tert-butyl), alkenyl group of 2 to 4 carbon atoms (e.g., vinyl, allyl, 1-methylvinyl, 2-methylvinyl), cycloalkyl groups of 3 to 6 carbon atoms (e.g., cyclopropyl, cyclobutyl, cyclopentyl, cyclohexyl), cycloalkenyl groups of 5 to 6 carbon atoms (e.g., cyclopentenyl, cyclohexenyl), aralkyl-groups of 7 to 8 carbon atoms (e.g., benzyl, α-methylbenzyl, phenethyl), phenyl group, alkoxy groups of about 1 to 4 carbon atoms (e.g., methoxy, ethoxy, propoxy, iso-propoxy, n-butoxy, iso-butoxy, sec-butoxy, tert-butoxy), phenoxy group, alkanoyl groups of 1 to 4 carbon atoms (e.g., formyl, acetyl, propionyl, n-butyryl, iso-butyryl), benzoyl group, alkanoyloxy groups of 1 to 4 carbon atoms (e.g., formyloxy, acetyloxy, propionyloxy, n-butyryloxy, isobutyryloxy), benzoyloxy group, carboxyl group, alkoxycarbonyl groups of 2 to 4 carbon atoms (e.g., methoxycarbonyl, ethoxycarbonyl, n-propoxycarbonyl, iso-propoxycarbonyl, n-butoxycarbonyl, isobutoxycarbonyl, t-butoxycarbonyl), carbamoyl group, carbamoyl groups N-monosubstituted by C$_{1-4}$ alkyl (e.g., N-methylcarbamoyl, N-ethylcarbamoyl, N-propylcarbamoyl, N-isopropylcarbamoyl, N-butylcarbamoyl), carbamoyl groups N,N-substituted by C$_{1-4}$ alkyl (e.g., N,N-dimethylcarbamoyl, N,N-diethylcarbamoyl, N,N- dipropylcarbamoyl, N,N-dibutylcarbamoyl), 1-pyrrolidinylcarbonyl, 1-piperidinylcarbonyl, N-methylpiperazinylcarbonyl, morpholinocarbonyl, halogen atoms (e.g., fluorine, chlorine, bromine, iodine), hydroxyl group, epoxy group, nitro group, cyano group, trifluoromethyl group, diazo group, amidino group, imino group, amino group, amino groups mono-substituted by $C_{1-4}$ alkyl (e.g., methylamino, ethylamino, propylamino, isopropylamino, butylamino), amino groups di-substituted by $C_{1-4}$ alkyl (e.g., dimethylamino, diethylamino, dipropylamino, diisopropylamino, dibutylamino), 5- or 6-membered cyclic amino groups (e.g., pyrrolidinyl, pyrrolinyl, pyrrolyl, imidazolyl, pyrazolyl, imidazolidinyl, piperidino, morpholino, dihydropyridyl, pyridyl, N-methylpiperazinyl, N-ethylpiperazinyl), alkanoylamido groups of 1 to 4 carbon atoms (e.g., formamido, acetamido, trifluoroacetamido, propionylamido, butyrylamido, isobutyrylamido), benzamido group, mercapto group, sulfo group, sulfino group, phosphono group, dihydroxyboryl group, sulfamoyl group, sulfamoyl groups N-monosubstituted by $C_{1-4}$ alkyl (e.g., N-methylsulfamoyl, N-ethylsulfamoyl, N-propylsulfamoyl, N-isopropylsulfamoyl, N-butylsulfamoyl), sulfamoyl groups N,N-disubstituted by $C_{1-4}$ alkyl (e.g., N,N-dimethylsulfamoyl, N,N-diethylsulfamoyl, N,N-dipropylsulfamoyl, N,N-dibutylsulfamoyl), 1-pyrrolidinylsulfonyl, 1-piperidinylsulfonyl, N-methyl-1-piperazinylsulfonyl, morpholinosulfonyl, alkylthio groups of 1 to 4 carbon atoms (e.g., methylthio, ethylthio, propylthio, isopropylthio, n-butylthio, sec-butylthio, tert-butylthio), phenylthio group, alkylsulfinyl groups of 1 to 4 carbon atoms (e.g., methylsulfinyl, ethylsulfinyl, propylsulfinyl, butylsulfinyl), phenylsulfinyl group, alkylsulfonyl groups of about 1 to 4 carbon atoms (e.g. methylsulfonyl, ethylsulfonyl, propylsulfonyl, butylsulfonyl), phenylsulfonyl, etc. Among these substituents, those susceptible of further substitution may be substituted by one or two alkyl groups of about 1 to 4 carbon atoms (e.g., methyl, ethyl, propyl, isopropyl, butyl, isobutyl, sec-butyl, tert-butyl), methoxy group, ethoxy group, halogen atoms (e.g., fluorine, chlorine, bromine, iodine) and/or water-soluble groups (e.g., hydroxyl, carboxyl, sulfo, phosphono, amidino, amino, methylamino, ethylamino, dimethylamino, diethylamino, morpholino, piperidyl, N-methylpiperazinyl, pyridyl, trimethylammonium, triethylammonium, pyridinium groups). In cases in which $R^3$, $R^4$, $R^5$ and $R^6$ each represents a protective group, as such a protective group, there are used, for example, acyl groups (e.g., formyl, acetyl, monochloroacetyl, dichloroacetyl, trichloroacetyl, trifluoroacetyl, benzoyl, o-nitrophenoxyacetyl, p-anisoyl), diacyl groups (e.g., succinoyl, phthaloyl), alkoxycarbonyl groups (e.g., methoxycarbonyl, ethoxycarbonyl, 2,2,2-trichloroethoxycarbonyl, β-methylsulfonylethoxycarbonyl, t-butoxycarbonyl, benzyloxycarbonyl, p-methoxybenzyloxycarbonyl, β-(p-toluenesulfonyl)ethoxycarbonyl), aryloxycarbonyl groups (e.g., phenoxycarbonyl, p-methoxyphenoxycarbonyl), thiophenoxycarbonyl group, aralkyl groups (e.g., benzyl, p-methoxybenzyl, p-chlorobenzyl, p-nitrobenzyl), trialkylsilyl groups (e.g., trimethylsilyl, t-butyldimethylsilyl), triarylmethyl groups (e.g., trityl, dimethoxytrityl), alkoxyalkyl groups (e.g., methoxymethyl, isopropyloxymethyl, tetrahydrofuranyl, tetrahydropyranyl), alkylthiomethyl groups (e.g., methylthiomethyl, benzylthiomethyl), alkylthio groups (e.g., methylthio, ethylthio), arylthio groups (e.g., phenylthio, aminophenylthio, methoxyphenylthio, nitrophenylthio), alkyl groups (e.g., methyl, ethyl, isopropyl, t-butyl), vinyl group, allyl group, aryls (e.g., phenyl, p-methoxyphenyl, p-chlorophenyl, 3,4-dimethoxyphenyl, 3,4,5-trimethoxyphenyl), phenacyl group, carbamoyl group, N-mono-substituted carbamoyl groups (e.g., N-methylcarbamoyl, N-ethylcarbamoyl, N-propylcarbamoyl, N-butylcarbamoyl, N-phenylcarbamoyl), N,N-di-substituted carbamoyl groups (e.g., N,N-dimethylcarbamoyl, N,N-diethylcarbamoyl, N,N-dipropylcarbamoyl, N,N-dibutylcarbamoyl), 1-pyrrolidinylcarbonyl, 1-piperidinylcarbonyl, N-methylpiperazinylcarbonyl, morpholinocarbonyl, sulfo group, alkylsulfonyl groups (e.g., methanesulfonyl, ethanesulfonyl), and arylsulfonyl groups (e.g., benzenesulfonyl, p-toluenesulfonyl). Preferable examples of said protective groups include, for example, formyl, acetyl, monochloroacetyl, trifluoroacetyl, benzoyl, p-anisoyl, phthaloyl, methoxycarbonyl, ethoxycarbonyl, 2,2,2-trichloroethoxycarbonyl, t-butoxycarbonyl, benzyloxycarbonyl, phenoxycarbonyl, benzyl, p-methoxybenzyl, p-chlorobenzyl, p-nitrobenzyl, t-butyldimethylsilyl, trityl, methoxymethyl, isopropyloxymethyl, tetrahydropyranyl, methyl, t-butyl, carbamoyl, N,N-dimethylcarbamoyl and sulfo.

As the group $R^1$, the more preferable scope is as follows:

$R^1$ is phenyl which has, at the ortho position and/or para position as a substituent, at least one group by the formula $-O-R^3$, $-S-R^4$,

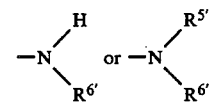

wherein $R^{3'}$ is alkyl of 5 to 24 carbon atoms, alkyl of 1 to 24 carbon atoms which is substituted or phenyl which may be substituted, $R^4$ is hydrogen or an alkyl or phenyl group which may be substituted, $R^{5'}$ and $R^{6'}$ are the same or different and each is alkyl of 5 to 24 carbon atoms, alkyl of 1 to 24 carbon atoms which is substituted or phenyl which may be substituted, whereby $R^5$ and $R^6$, together with the adjacent nitrogen atom, may form a cyclic amino group which may be substituted, and $R^{3'}$, $R^4$, $R^{5'}$ and $R^{6'}$ each may represent a protective group.

In cases in which the phenyl represented by the above $R^1$ has, at the ortho position and/or para position as a substituent, at least one group represented by $-O-R^3$, $-S-R^4$ or

(wherein $R^3$, $R^4$, $R^5$ and $R^6$ are as defined hereinbefore), preferred examples of such a substituent include, for example, hydroxy, methoxy, ethoxy, propyloxy, butyloxy, octyloxy, phenoxy, benzyloxy, mercapto, methylthio, ethylthio, propylthio, butylthio, decylthio, phenylthio, amino, methylamino, ethylamino, propylamino, butylamino, dimethylamino, diethylamino, dipropylamino, dibutylamino, phenylamino, formyloxy, acetyloxy, propionyloxy, butyloxy, benzoyloxy, formamido, acetamido, trifluoroacetamido and benzamido.

Preferable examples of the 5- or 6-membered ring which $R^5$ and $R^6$ together with the adjacent nitrogen atom form include, for example, pyrrolidinyl, pyrrolyl, imidazolyl, morpholino, piperidino, N-methylpiperazinyl and N-ethylpiperazinyl.

The more preferable examples of such a substituent include octyloxy, phenoxy, benzyloxy, mercapto, methylthio, ethylthio, propylthio, butylthio, decylthio, phenylthio, phenylamino, formyloxy, acetyloxy, propionyloxy, butyryloxy, benzoyloxy, formamido, acetamido, trifluoroacetamido, benzamido, pyrrolidinyl, pyrrolyl, imidazolyl, morpholino, piperidino, N-methylpiperazinyl and N-ethylpiperazinyl.

The further preferable examples of such a substituent include mercapto, methylthio, acetylthio, propionyloxy, butyryloxy, acetamido, trifluoroacetamido, pyrrolyl, morpholino and N-methylpiperazinyl.

In cases where the phenyl represented by $R^1$, which, as described hereinbefore, has at least one group represented by the formula $-O-R^3$, $-S-R^4$ or

(wherein $R^3$, $R^4$, $R^5$ and $R^6$ are as defined hereinbfore) at the ortho position and/or para position, has two or three of the above groups at the ortho position and/or para position, the said groups may be the same or different.

In the above formula, the group with a molecular weight of up to about 200 which the phenyl represented by $R^1$ may have as a substituent at a position other than the ortho position and/or para position having at least one substituent of the formula $-O-R^3$, $-S-R^4$ or

includes, for example, alkyl groups of 1 to 12 carbon atoms (e.g., methyl, ethyl, propyl, isopropyl, butyl, isobutyl, sec-butyl, tert-butyl, pentyl, isopentyl, hexyl, isohexyl, heptyl, octyl, nonyl, decyl, undecyl, dodecyl), alkenyl groups of 2 to 12 carbon atoms (e.g., vinyl, allyl, 1-methylvinyl, 2-methylvinyl, 1-octenyl, 1-decenyl), cycloalkyl groups of 3 to 12 carbon atoms (e.g., cyclopropyl, cyclobutyl, cyclopentyl, cyclohexyl, cycloheptyl, cyclooctyl, adamantyl), cycloalkeny groups of 3 to 8 carbon atoms (e.g., cyclopentenyl, cyclohexenyl, cycloheptenyl, cyclooctenyl, cyclopetandienyl, cyclohexadjenyl, cycloheptadienyl, cyclooctadienyl), aralkyl groups of 7 to 13 carbon atoms (e.g., benzyl, α-methylbenzyl, phenethyl, diphenylmethyl), aryl groups of 6 to 10 carbon atoms (e.g. phenyl, naphthyl, alkoxy groups of 1 to 4 carbon atoms (e.g., methoxy, ethoxy, propoxy, iso-propoxy, n-butoxy, iso-butoxy, sec-butoxy, tert-butoxy), phenoxy group, alkanoyl groups of 1 to 4 carbon atoms (e.g., formyl, acetyl, propionyl, n-butyryl, iso-butyryl), benzoyl group, alkanoyloxy groups of 1 to 4 carbon atoms (e.g., formyloxy, acetyloxy, propionyloxy, n-butyryloxy, iso-butyryloxy), benzoyloxy group, carboxy group, alkoxycarbonyl groups of 2 to 4 carbon atoms (e.g., methoxycarbonyl, ethoxycarbonyl, n-propoxycarbonyl, iso-propoxycarbonyl, n-butoxycarbonyl, isobutoxycarbonyl, t-butoxycarbonyl), cabamoyl group, carbamoyl groups N-monosubstituted by $C_{1-4}$ alkyl (e.g., N-methylcarbamoyl, N-ethylcarbamoyl, N-propylcarbamoyl, N-isopropylcarbamoyl, N-butylcarbamoyl), carbamoyl groups N,N-disubstituted by $C_{1-4}$ alkyl (e.g., N, N-dimethylcarbamoyl, N,N-diethylcarbamoyl, N,N-dipropylcarbamoyl, N,N-dibutylcarbamoyl), 1-pyrrolidinylcarbonyl, 1-piperidinylcarbonyl, N-methylpiperazinylcarbonyl, morpholinocarbonyl, halogen atoms (e.g., fluorine, chlorine, bromine, iodine), hydroxy group, epoxy group, nitro group, cyano group, trifluoromethyl group, diazo group, amidino group, imino group, amino group, amino groups mono-substituted by $C_{1-4}$ alkyl (e.g., methylamino, ethylamino, propylamino, isopropylamino, butylamino), amino groups disubstituted by $C_{1-4}$ alkyl (e.g., dimethylamino, diethylamino, dipropylamino, diisopropylamino, dibutylamino), 5- or 6-membered cyclic amino groups (e.g., pyrrolidinyl, pyrrolinyl, pyrrolyl, imidazolyl, pyrazolyl, imidazolidinyl, piperidino, morpholino, dihydropyridiyl, pyridyl, N-methylpiperazinyl, N-ethylpiperazinyl), alkanoylamino groups of 1 to 4 carbon atoms (e.g., formamido, acetamido, trifluoroacetamido, propionylamido, butyrylamido, isobutyrylamido), benzamido group, mercapto group, sulfo group, sulfino group, phosphono group, dihydroxyboryl group, sulfamoyl group sulfamoyl N-mono-substituted by $C_{1-4}$ alkyl (e.g., N-methylsulfamoyl, N-ethylsulfamoyl, N-propylsulfamoyl, N-isopropylsulfamoyl, N-butylsulfamoyl), sulfamoyl groups N,N-disubstituted by $C_{1-4}$ alkyl (e.g., N,N-dimethylsulfamoyl, N,N-diethylsulfamoyl, N,N-dipropylsulfamoyl, N,N-dibutylsulfamoyl), 1-pyrrolidinylsulfonyl, 1-piperidinylsulfonyl, N-methylpiperazinylsulfonyl, morpholinosulfonyl, alkylthio groups of 1 to 10 carbon atoms (e.g., methylthio, ethylthio, propylthio, isopropylthio, n-butylthio, sec-butylthio, pentylthio, isopentylthio, hexylthio, isohexylthio, heptylthio, octylthio, nonylthio, decylthio), phenylthio group, alkylsulfinyl groups of 1 to 10 carbon atoms (e.g., methylsuflinyl, ethylsulfinyl, propylsulfinyl, butylsulfinyl, pentylsulfinyl, hexylsulfinyl, heptylsulfinyl, octylsulfinyl, nonylsulfinyl, decylsulfinyl), phenylsulfinyl group, alkylsulfonyl groups of 1 to 8 carbon atoms (e.g., methylsulfonyl, ethylsulfonyl, propylsulfonyl, butylsulfonyl, pentylsulfonyl, hexylsulfonyl, heptylsulfonyl, octylsulfonyl), phenylsulfonyl group, etc.

Off these substituents, those capable of undergoing further substitution may be substituted by one or two of alkyl groups of 1 to 4 carbon atoms (e.g., methyl, ethyl, propyl, isopropyl, butyl, isobutyl, sec-butyl, tert-butyl), methoxy group, ethoxy group, halogen atoms (e.g., fluorine, chlorine, bromine, iodine) and/or water-soluble groups (e.g., hydroxy, carboxyl, sulfo, phosphono, amidino, amino, methylamino, ethylamino, dimethylamino, diethylamino, morpholino, piperidyl, N-methylpiperazinyl, pyridyl, trimethylammonium, triethylammonium, pyridinium groups).

Preferable examples of the group with a molecular weight of up to about 200 which may be carried by the phenyl represented by $R^1$ as mentioned above include, for example, methyl, ethyl, propyl, butyl, vinyl, allyl, cyclopentyl, cyclohexyl, benzyl, phenyl, hydroxy, methoxy, ethoxy, propoxy, butoxy, phenoxy, formyl, acetyl, benzoyl, acetyloxy, carboxy, methoxycarbonyl, ethoxycarbonyl, propoxycarbonyl, carbamoyl, halogens, nitro, cyano, trifloromethyl, amino, methylamino, ethylamino, propylamino, isopropylamino, butylamino, dimethylamino, diethylamino, dipropylamino, diisopropylamino, dibutylamino, pyrrolidinyl, morpholino, piperidino, N-methylpiperazinyl, N-ethylpiperazinyl, sulfo, phosphono, sulfamoyl, N-methylsulfamoyl, N-ethylsulfamoyl, N-propylsulfamoyl, N-isopropylsulfamoyl, N-butylsulfamoyl, N,N-dimethylsulfamoyl, N,N-diethylsulfamoyl, N,N-dipropylsulfamoyl, N,N-dibutylsulfamoyl, methylthio, ethylthio, propylthio, butylthio, phenylthio, methylsulfonyl, ethylsulfonyl or phenylsulfonyl.

The phenyl represented by $R^1$ has at least one group —O—$R^3$, —S—$R^4$ or

(wherein $R^3$, $R^4$, $R^5$ and $R^6$ are as defined hereinbefore) at the ortho position and/or para position, but may also have at least one group —O—$R^3$, —S—$R^4$ or

being substituted at the ortho position and/or para position and the above-described group or groups with a molecular weight of up to about 200 being substituted at the remaining ortho position and/or para position.

The protective group in the amino group which may be protected as represented by $R^2$ includes, for example, acyl group, alkoxycarbonyl groups, aryloxycarbonyl groups, N-substituted carbamoyl groups, thioalkoxycarbonyl groups, thioaryloxycarbonyl groups, arylmethyl groups, N,N-dialkylaminomethylene groups, diphenylaminomethylene, phosphoryl group which may have one or two benzyl, sulfo, alkylsulfonyl, arylsulfonyl group, and tri($C_{1-4}$alkyl)silyl group.

The acyl groups as the said protective group are preferably those with a molecular weight of not more than about 400, and their specific examples include, for example, alkanoyl groups and aroyl groups. The above-described alkanoyl groups are preferably those of 1 to 18 carbon atoms, and their examples include, for example, formyl, acetyl, monochloroacetyl, dichloroacetyl, trichloroacetyl, trifluoroacetyl, propionyl, butyryl, isobutyryl, succinyl, valeryl, isovaleryl, pivaloyl, hexanoyl, heptanoyl, octanoyl, 2-ethylhexanoyl, nonanoyl, decanoyl, undecanoyl, tridecanoyl, tetradecanoyl, pentadecanoyl, hexadecanoyl, heptadecanoyl and octadecanoyl, with those of 1 to 10 carbon atoms being among others conveniently used. The above-described aroyl groups are preferably those of 7 to 12 carbon atoms, and their examples include, for example, benzoyl, o-anisoyl, o-cyanobenzoyl, o-nitrobenzoyl, toluoyl, phthaloyl and naphthoyl, with benzoyl group being among others conveniently employed.

The alkoxycarbonyl groups are preferably those of 1 to 15 carbon atoms, and their examples include, for example, methoxycarbonyl, ethoxycarbonyl, 2,2,2-trichloroethoxycarbonyl, β-methylsulfonylethoxycarbonyl, propoxycarbonyl, isopropoxycarbonyl, butoxycarbonyl, sec-butoxycarbonyl, tert-butoxycarbonyl, benzyloxycarbonyl, p-methoxybenzyloxycarbonyl, 2-(p-xenyl)isopropoxycarbonyl and β-(p-toluenesulfonyl)ethoxycarbonyl, with tert-butoxycarbonyl benzyloxycarbonyl, etc. being among others conveniently used. The aryloxycarbonyl groups are preferably those of 6 to 12 carbon atoms, and their examples include, for example, phenoxycarbonyl, p-methoxyphenoxycarbonyl, α-naphthoxycarbonyl and β-naphthoxycarbonyl. As the N,N-substituted carbamoyl groups, there are used, for example, piperidinocarbonyl and N,N-diphenylcarbamoyl. The thioalkoxycarbonyl groups are preferably those of 1 to 7 carbon atoms, and their examples include, for example, thiomethoxycarbonyl, thioethoxycarbonyl, thiopropoxycarbonyl, thiobutoxycarbonyl and thiobenzyloxycarbonyl, with thiobenzyloxycarbon, etc. being among others conveniently employed. As the thioaryloxycarbonyl groups, there are used, for example, thiophenoxycarbonyl, thio-α-naphthoxycarbonyl and thio-β-naphthoxycarbonyl. As the arylmethyl groups, there are used, for example, benzyl, p-methoxybenzyl, 3,4,5-trimethyoxybenzyl, di(p-methoxybenzyl)methyl, trityl and monomethoxytrityl. As the N,N-dialkylaminomethylene groups, there are used, for example, dimethylaminomethylene, diethylaminomethylene, dipropylaminomethylene and diphenylaminomethylene. As the phosphoryl groups, there are used, for example, p-nitrobenzylphosphoryl, p-bromobenzylphosphoryl, dibenzylphosphoryl, di(p-nitrobenzyl)phosphoryl, di(o-bromobenzyl)phosphoryl and di(p-iodobenzyl)phosphoryl. The sulfonyl groups include, for example, sulfo, benzylsulfonyl, phenacylsulfonyl groups suflonyl and toluenesulfonyl. The trialkylsilyl groups include, for example, trimethylsilyl and tert-butyldimethylsilyl.

Preferable examples of the protective groups at the amino group which may be protected as represented by $R^2$ include formyl, acetyl, monochloroacetyl, trifluoroacetyl, octanoyl, 2-ethylhexanoyl, benzoyl, p-anisoyl, phthaloyl, methoxycarbonyl, ethoxycarbonyl, 2,2,2trichloroethoxycarbonyl, tert-butoxycarbonyl, benzyloxycarbonyl, β-methylsulfonylethoxycarbonyl, phenoxycarbonyl, dimethylaminomethylene, etc.

The more preferable examples of the protective groups include acetyl, monochloroacetyl, octanoyl, benzoyl and dimethylaminomethylene.

The compound (I) of the present invention can be readily produced, for example, by the following method of synthesis.

Thus, 7-deazapurine derivatives of the formula (I) can be obtained by subjecting a compound of the formula:

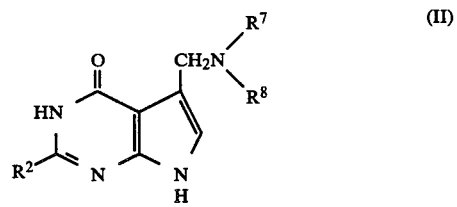

[wherein $R^2$ is as defined hereinbefore; $R^7$ and $R^8$ each is an alkyl, alkenyl or aralkyl group having a methylene group in the α position, or both of $R^7$ and $R^8$, together with the adjacent nitrogen atom, may form a cyclic amino group] or its salt to a substitution reaction with an amine of the formula:

$$H_2N—R^1 \qquad (III)$$

[wherein R¹ is as defined hereinbefore] or its salt, and subsequently subjecting the reaction product to a deprotection reaction, if desired, in cases R² is a protected amino group.

The individual groups represented by $R^7$ and $R^8$ may be the same or different, and the alkyl group having a methylene group in the α position includes those of 1 to 10 carbon atoms, such as methyl, ethyl, propyl, isopropyl, butyl, isobutyl, tert-butyl, pentyl, isopentyl, hexyl, isohexyl, heptyl, octyl, nonyl and decyl, with alkyl groups of 1 to 6 carbon atoms being among others conveniently used. The alkenyl groups having a methylene group in the α position include, for example, those of 3 to 13 carbon atoms, such as allyl(2-propenyl), 2-butenyl, 2-pentenyl, 2-hexenyl, 4-propyl-2-pentenyl, cinnamyl and 2-nonyl-2-butenyl, and among others, alkenyl groups of 3 to 9 carbon atoms are conveniently employed. These alkyl and alkenyl groups may have a substituent or substituents in any position other than the α position, and such a substituent or substituents include alkyl groups of 1 to 4 carbon atoms (e.g., methyl, ethyl, propyl, isoproyl, butyl, isobutyl, sec-butyl, tert-butyl), alkoxy groups of 1 to 4 carbon atoms (e.g., methoxy, ethoxy, propoxy, iso-propoxy, n-butoxy, iso-butoxy, sec-butoxy, tert-butoxy), alkanoyl groups of 1 to 4 carbon atoms (e.g., formyl, acetyl, propionyl, n-butyryl, iso-butyryl), hydroxy group, nitro group, halogens (e.g., fluorine, chlorine, bromine, iodine), cyano group, trifluoromethyl group, dialkylamino groups (e.g., dimethylamino, diethylamino, dipropylamino, diisopropylamino, dibutylamino), alkanoylamido groups (e.g., formamido, acetamido, propionylamido, butyrylamido, isobutyrylamido), etc.

The aralkyl groups having a methylene group in the α position as represented by $R^7$ and $R^8$ include those of about 7 to 12 carbon atoms, such as benzyl, phenethyl, 3-phenylpropyl, naphthylmethyl and naphthylethyl, and among others, benzyl group is conveniently used. These aralkyl groups may also have a substituent or substituents in the alkylene chain and/or aryl (phenyl) ring moiety other than the α position, and these substituents include the groups as exemplified in the above for the alkyl and alkenyl groups.

The cyclic amino group which $R^7$ and $R^8$ together with the adjacent nitrogen atom form includes, for example, 5- or 6-membered cyclic amino groups, and they may carry a second cyclic hetero atom (e.g., N, O) in addition to the above nitrogen atom. Such cyclic amino groups include, for example, 1-pyrrolidinyl, 1-pyrrolinyl, 1-imidazolidinyl, 1-imidazolinyl, 1-pyrazolidinyl, 1-pyrazolinyl, morpholino, piperidino and 1-piperazinyl, and these cyclio amino groups may have a substituent or substituents at any position other than the position (α position) adjacent to the nitrogen atom; such substituents include the groups as exemplified in the above for the alkyl and alkenyl groups.

The substitution reaction between the compound (II) or a salt thereof and the compound (III) or a salt thereof as mentioned above can be effected, for example, by allowing both of the compounds to react at a ratio of the compound (III)/the compound (II) in the range of about 1 to 20 (molar ratio) in the absence or presence of a suitable reaction solvent employed at a reaction temperature within the range of about 0° C. to the boiling point of such a reaction solvent, preferably about 20° to 100° C., for about 1 hour to 5 days. In case the compound (II) is converted to a quaternary salt, such as salts with methyl bromide, methyl iodide, methyl methanesulfonate, methyl benzenesulfonate and methyl p-toluenesulfonate, the reaction can be allowed to proceed under milder reaction conditions. In such a case, the resultant quaternary salt of the compound (II) may be isolated or subjected, directly without elimination, to the substitution reaction with the compound (III). As the reaction solvent to be used in the substitution reaction between the compound (II) and the compound (III), there are used, for example, water, methanol, ethanol, propanol, butanol, pentanol, tetrahydrofurane, dioxane, acetonitrile, pyridine, dimethylformamide, dimethylsulfoxide, sulfolane or suitable solvent mixtures thereof. In cases in which the compound (II) or the compound (III) is used in the form of a salt, the objective compound (I) or its salt can be advantageously produced by adjusting to the optimal pH (normally, to a pH of about 5 to 13) with a base (e.g., sodium hydroxide, potassium hydroxide, lithium hydroxide, barium hydroxide, triethylamine, N-methylmorpholine) or a salt (e.g., sodium chloride, potassium chloride, calcium chloride, sodium carbonate, potassium carbonate, sodium hydrogencarbonate).

When in the desired compound (I), the group which is carried on the phenyl represented by $R^1$ is a hydroxy, amino, mono-substituted amino, mercapto, carboxy, sulfo, phosphono or formyl group or $R^3$, $R^4$, $R^5$ or $R^6$ each is a group containing as a substituent a hydroxy, amino, monosubstituted amino, mercapto, carboxy, sulfo, phosphono or formyl group, the group $R^1$ in the compound (III) may be one of those having these substituents protected with protective groups.

In cases in which the said substituent is a hydroxy, amino, mono-substituted amino or mercapto group, the above described protective groups include the protective groups as exemplified in the above when $R^3$, $R^4$, $R^5$ or $R^6$ each represents a protective group.

In cases in which the above protective group is a carboxy, sulfo or phosphono group, these groups can be converted to ester groups (e.g., methyl ester, ethyl ester, t-butyl ester, phenyl, benzyl ester), and in the case of it being a formyl group, the said formyl group can be converted to an acetal group (e.g., methyl acetal, ethyl acetal), to provide protection.

The procedure of introducing the said protective groups and the procedure of deprotecting the said protective groups are carried out by the methods known per se [J. F. W. McOmie, Protective Groups in Organic Chemistry. Plenum Press, London and New York (1973)].

With reference to a substituent susceptible to chemical conversion, after the compound (I) is produced, only its substituent moiety can be allowed to undergo chemical conversion by the per se known method to produce the compound (I) having the objective substituent. Examples of such substituent conversion include, for example, conversions from nitro group into amino group, from alkanoylamido group into amino group, from amino group into mono-substituted amino group, di-substituted amino group, alkanoylamido group, halogen atom, hydroxyl group or cyano group, from cyano group into carbamoyl group, alkoxycarbonyl group or carboxy group, from hydroxy group into alkoxy group or alkanoyloxy group and from alkoxy group into hydroxy group [refer to S. H. Pyne, J. B. Hendrickson, D. J. Cram and G. S. Hammond, "Organic Chemistry" (4th edition) [I] and [II], Hirokawa Shoten Co. (1982)].

When the compound (I) wherein $R^2$ is a protected amino group is produced, such a compound can be subjected to a deprotection reaction to obtain the compound wherein $R^2$ is $-NH^2$. The said deprotection reaction can be carried out readily by the per se known methods [J. F. W. McOmie, Protective Groups in Organic Chemistry, Plenum Press, London and New york (1973)].

The starting compounds (II) to be used in the above described methods can be readily produced by the methods known in the literature [refer to the Japanese Unexamined Patent Publication No. 157790/1983 which corresponds to U.S. Pat. No. 4,571,423].

As another starting compounds (III), there are used known compounds and compounds which are produced in accordance with the method for producing them [R. B. Wagner and H. D. Zook, Synthetic Organic Chemistry, John Wiley & sons, Inc. (1953)].

The 7-deazapurine derivatives (I) as produced in accordance with the method of the present invention can be isolated from the reaction mixture by usual separation and purification means, such as concentration, solvent extraction, chromatography and recrystallization. When the compounds (I) are obtained in the free form, they may be converted to forms of the pharmaceutically acceptable salt. Pharmaceutically acceptable salts of the compounds (I) include, for example, salts with such mineral acids as hydrochloric acid, sulfuric acid, nitric acid, phosphoric acid and boric acid, salts with such organic acids as oxalic acid, tartaric acid, acetic acid, trifluoroacetic acid, methanesulfonic acid, benzenesulfonic acid, p-toluenesulfonic acid and camphorsulfonic acid, and quaternary salts with methyl bromide, methyl iodide, methyl methanesulfonate, methyl benzenesulfonate, p-sulfonates, etc.

In cases in which the compounds are obtained in the forms of salts other than quaternary salts, these can be converted into the free form, if desired. Such a conversion can be readily conducted by subjecting a salt of the compound (I) to the normally employed procedure, such as neutralization reaction and anion exchange chromatography.

The thus-obtained compounds (I) or salts thereof inhibit markedly a growth of cultured L5178Y cells in vitro as well as a growth of Meth A, Sarcoma, etc. in vivo.

As described hereinafter, it can be appreciated that the compounds (I) of the present invention or salts exhibit marked antitumor activity.

Also, the compounds (I) or salts thereof, when intraperitoneally administered to mice in a dose of 200 mg/kg, do not cause any death.

Therefore, the compounds (I) or salts thereof can be used as an antitumor agent for the purpose of treatment of tumors in warm-blooded animals, especially mammals (e.g., mice, rats, cats, dogs, rabbits, etc.)

In using as an antitumor agent, they can be administered orally or parenterally, either as such or in the dosage forms, such as powders, granules, tablets, capsules, suppositories and injections, which are prepared in the conventional manner with use of pharmacologically acceptable carriers, excipients, diluents, etc. Their dose varies with the animal to be treated, the conditions and severity of the disease, the kind of the compounds, the route of administration and other factors, and generally comprises about 10 to 200 mg/kg of body weight per day as the compound (I) in the case of oral administration and about 10 to 100 mg/kg of body weight per day as the compound (I) in the case of parenteral administration.

Furthermore, the compounds (I) or salts thereof possess antiviral and antimicrobial activities against various viruses and microbes, such as *Xanthomonas oryzae, Pyricularia oryzae, Escherichia coli* or *Serratia marcescens*. Since the compounds (I) are low in toxicity as described above, the compound (I) can be employed as an antiviral agent, antimicrobial agent or disinfectant intended for the prevention and treatment of viral and bacterial infectious diseases in warm-blooded animals, particularly in mammals (e.g., mice, rats, cats, dogs, rabbits, human).

The compounds (I) or salts thereof, in using them as an antimicrobial agent or disinfectant, are formulated e.g. into liquid preparations containing the compound (I) or a salt thereof in the concentration of about 0.5 to 500 mg/ml in water, an aqueous solution such as isotonic glucose solution and Ringer solution, or a nonaqueous solution such as a vegetable (e.g., cotton seed, peanut, corn, sesame) fatty oil, and such preparations can be applied to the hand, foot, ear and other parts of mammals for sterilization and disinfection of such applied parts.

The compounds (I) or salts thereof, after being formulated into tablets containing about 0.5 to 500 mg of the compound (I) or a salt thereof in an excipient such as lactose, starch and talc, can be used orally in the prevention and treatment of viral and bacterial infectious diseases in mammals. In such a case, the dose is about 10 to 200 mg/kg of body weight per day as the compound (I).

Moreover, the compounds (I), particularly the compounds (I) wherein $R^2$ is a protected amino group, can be used as an intermediate for the synthesis of useful drugs.

The Experimental Examples and Examples are described below to illustrate the present invention, but it is to be understood that the present invention should not be limited to them.

Described below are biological experimental data of the compounds (I) of the present invention.

EXPERIMENTAL EXAMPLE 1

Experiment on the uptake into tRNA of the compound obtained in Example 1 to be described hereinafter:

[$^3$H] guanine labeled tRNA* (8000 cpm), 70 mM of hydrochloride, 60 mM of magnesium chloride, 0.5 unit of rat liver tRNA-guanine transglycosylase and 0.02 OD$_{260}$ of the compound obtained in Example 1 to be described hereinafter were prepared to the total volume of 100 μl, and the reaction was allowed to proceed at 37° C. for 17 hours. The reaction solution was applied to a Whatman 3 MM filter paper (produced by Whatman Co., U.S.A.), which was washed three times with a 5% aqueous solution of trichloroacetic acid and once successively with ethanol/ether (1:1) and ether alone. After drying, the uptake of the test compound was determined in a toluenic scintillation fluid, and it was found that the compound of Example 1 had been taken up in 120% of tRNA.

(*) tRNA with the first letter of its anticodon labeled with [$^3$H]-guanine.

EXPERIMENTAL EXAMPLE 2

The uptake of the compound of Example 2 (2) into tRNA was found to be 140% as determined in the same manner as Experimental Example 1.

EXPERIMENTAL EXAMPLE 3

1×10⁴ L5178Y mouse tumor cells were suspended in 2 ml of a RPMI-1640 medium (produced by Nissui Pharmaceutical Co. of Japan) containing 10% of bovine fetal serum, 20 μM of 2-mercaptoethanol and 100 μg/ml of Kanamycin, and incubated at 37° C. for 24 hours before addition of the drug. Using the above culture fluid as a diluent, the compound as obtained in Example 3 to be described hereinafter was diluted $\frac{1}{4}$-fold in a series of 5 stages and added to the culture medium in such a manner that the maximum concentration of the compound might be 200 μg/ml. The dilutions were further incubated for 72 hours, at the end of which time the cells were counted with use of a counter and the IC$_{50}$ (50% growth inhibitory concentration) was calculated with the count for the non-treated control group being taken as 100%. The IC$_{50}$ value was 2.0 μg/ml.

EXPERIMENTAL EXAMPLE 4

5×10⁴ Meth A tumor cells were subcutaneously transplanted into a BALB/c mouse weighing 20 g, and starting with the fourth day after transplantation, a solution of the compound as obtained in Example 3 to be described hereinafter in 0.1 ml of distilled water prepared in such a way that a dose might be 100 mg/kg was intraperitoneally injected into the mouse once a day for 14 consecutive days. On the 35th day after transplantation, the tumor node was enucleated and its weight (T) was measured. Comparison of the weight (C) of the non-treated control group indicated that the compound inhibited a growth of tumor. The tumor inhibition rate (T/C) reached 36%.

EXAMPLE 1

Production of 2-amino-5-(2-methoxyphenylaminomethyl)pyrrolo[2,3-d]pyrimidin -4-one 5-N,N-Dibenzylaminomethyl-2-octanoylaminopyrrolo-[2,3-d]pyrimidin -4-one(1.95 g) and o-anisidine (3.1 g) are suspended/dissolved in a mixed solution [3:2, 100 ml) of ethanol/tetrahydrofuran, and the reaction is allowed to proceed at 80° C. for 24 hours with stirring. The reaction solution is cooled to room temperature, and the resulting precipitate is collected by filtration, washed with methanol and ethanol successively and dried to give 5-(2-methoxyphenylaminomethyl)-2-octanoylaminopyrrolo[2,3-d]pyrimidin-4-one (1.35 g).

IR (KBr): ν 3230, 2960, 1680, 1660, 1640, 1585, 1515, 1440, 1245, 1120, 820 cm⁻¹.

The compound (1.06 g) is suspended in a mixed solution (1:1, 800 ml) of methanol/tetrahydrofuran, and aqueous concentrated ammonia (100 ml) is added to the suspension, followed by stirring at room temperature for 6 days. The reaction solution is concentrated to dryness under reduced pressure, and after methanol, tetrahydrofuran and ethyl ether are added to the residue, the resulting precipitate is collected by filtration to give the objective compound (0.623 g).

NMR (DMSO-d$_6$): δ3.70(s,3H), 4.22(d,2H), 6.40-6.83(m,5H).

IR: ν 1665, 1600, 1510, 1220 cm⁻¹.

EXAMPLE 2

By following a procedure similar to that of Example 1, 5-N,N-dibenzylaminomethyl-2-n-octanoylaminopyrrolo[2,3-d]pyrimidin 4-one (4 mmole) is reacted with various amines (III, 20 mmole) to give the corresponding 7-deazapurine derivatives (I) as shown in the following, whereby among the physico-chemical properties stated, NMR refers to spectra measured at 90 MHz using DMSO-d$_6$ as a solvent and IR refers to spectra recorded with KBr employed as a diluent. (1) Objective compound: 2-Amino-5-(2,4-dimethoxyphenylaminomethyl)pyrrolo[2,3-d]pyrimidin 4-one.

Yield: 0.425 g

Properties: NMR: δ 3.68(s,3H), 3.72(s,3H), 4.17(d,2H), 6.17-6.45(m,2H), 6.47(t,1H), 6.55(s,1H). IR: ν 1658, 1615, 1440, 1220 cm⁻¹.

Compound (III):

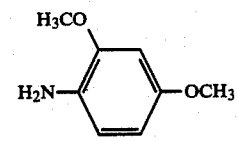

(2) Objective compound: 2-Amino-5-(3,4,5-trimethoxyphenylaminomethyl)pyrrolo[2,3-d]pyrimidin 4-one.

Yield: 0.795 g

Properties: NMR: δ 3.78(s,9H), 4.18(d,2H), 5.86(s,2H), 6.53(s,1H). IR: ν 1660, 1615, 1590, 1230 cm⁻¹.

Compound (III):

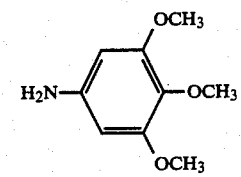

(3) Objective compound: 2-Amino-5-(5-chloro-2-hydroxyphenylaminomethyl)pyrrolo[2,3-d]pyrimidin 4-one.

Yield: 0.327 g

Properties: NMR: δ 4.20(d,2H), 6.30-6.80(m,4H). IR: ν 1653, 1615, 1500, 1210 cm⁻¹.

Compound (III):

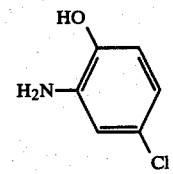

(4) Objective compound: 2-Amino-5-(2,4-dihydroxyphenylaminomethyl)pyrrolo[2,3-d]pyrimidin 4-one.

Yield: 0.285 g

Properties: NMR: δ 4.17(d,2H), 6.31(d,1H), 6.54(s,1H), 6.67(d,1H), 7.24(d,1H). IR: ν 1653, 1595, 1220 cm⁻¹.

Compound (III):

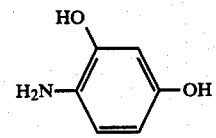

(5) Objective compound: 2-Amino-5-(2-mercaptophenylaminomethyl)pyrrolo[2,3-d]pyrimidin-4-one.
Yield: 0.108 g
Properties: NMR: δ 4.25(d,2H), 6.43–7.27(m,5H). IR: ν 1655, 1470, 1300 cm⁻¹.
Compound (III):

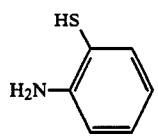

(6) Objective compound: 2-Amino-5-(5-N,N-diethylsulfamoyl-2-methoxyphenylamino)pyrrolo[2,3-d]pyrimidin 4-one.
Yield: 0.463 g
Properties: NMR: δ 1.10(t,6H), 3.17(q,4H), 3.86(s,3H), 4.22(d,2H), 6.55(s,1H). IR: ν 1660, 1590, 1150 cm⁻¹.
Compound (III):

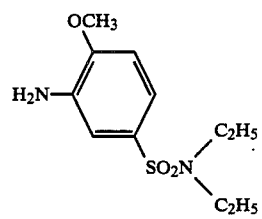

(7) Objective compound: 2-Amino-5-(4-amino-3-sulfophenylaminomethyl)pyrrolo[2,3-d]pyrimidin 4-one.
Yield: 0.312 g
Properties: NMR: δ 4.27(d,2H), 6.55(s,1H), 6.87(s,2H), 7.23(s,2H).
IR: ν 1660, 1590, 1245, 1185 cm⁻¹.
Compound (III):

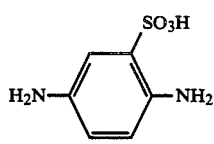

(8) Objective compound: 2-Amino-5-(4-methoxy-2-nitrophenylaminomethyl)pyrrolo[2,3-d]pyrimidin-4-one.
Yield: 0.376 g
Properties: NMR: δ 3.72(s,3H), 4.34(d,2H), 6.57(s,1H), 6.89–7.14(m,2H), 7.45(s,1H). IR: ν 1665, 1615, 1515, 1430 cm⁻¹.
Compound (III):

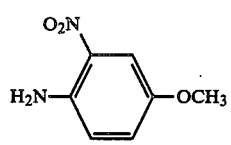

(9) Objective compound: 2-Amino-5-(4-amino-3-nitrophenylaminomethyl)pyrrolo[2,3-d]pyrimidin-4-one.
Yield: 0.486 g
Properties: NMR: δ 4.22(d,2H), 6.53(s,1H), 6.84(s,2H), 7.25(s,2H). IR: ν 1660, 1625, 1590, 1335 cm⁻¹.
Compound (III):

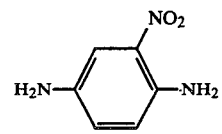

(10) Objective compound: 2-Amino-5-(4-N-phenylaminophenylaminomethyl)pyrrolo[2,3-d]pyrimidin-4-one.
Yield: 0.796 g
Properties: NMR: δ 4.18(d,2H), 6.48(s,1H), 6.50–7.25(m,9H). IR: ν 1660, 1590, 1445 cm⁻¹.
Compound (III):

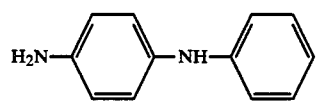

(11) Objective compound: 2-Amino-5-{4-(4-amino-3-methoxyphenyl)-2-methoxyphenylaminomethyl}pyrrolo[2,3-d]pyrimidin-4-one.
Yield: 0.725 g
Properties: NMR: δ 3.85(s,3H), 3.87(s,3H), 4.17(d,2H), 6.52(s,1H), 6.61–7.08(m,6H). IR: ν 1660, 1590, 1500, 1230 cm⁻¹.
Compound (III):

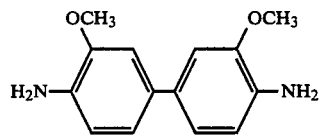

(12) Objective compound: 2-Amino-5-{4-(4-aminophenoxy)phenylaminomethyl}pyrrolo[2,3-d]pyrimidin-4-one
Yield: 0.812 g
Properties: NMR: δ 4.20(d,2H), 6.52(s,1H), 6.63(s,8H). IR: ν 1655, 1590, 1230 cm⁻¹.
Compound (III):

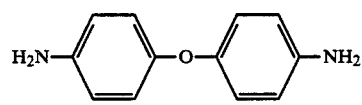

(13) Objective compound: 2-Amino-5-{4-[4-chlorobenzyloxy)phenylaminomethyl}pyrrolo[2,3-d]pyrimidin-4-one
Yield: 1.10 g
Properties: NMR: δ 4.13(d,2H), 4.93(s,2H), 6.50(d,1H), 6.53 (d,2H), 6.73(d,2H), 7.40(s,4H). IR: ν 3380, 1670, 1640, 1515, 1225 cm⁻¹.
Compound (III):

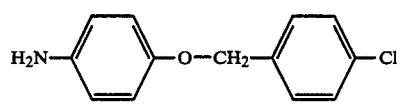

(14) Objective compound: 2-Amino-5-(4-pyrrolidinylphenylaminomethyl)pyrrolo[2,3-d]pyrimidin-4-one Yield: 0.604 g Properties: NMR: δ 1.65(m,4H), 2.91(m,4H), 4.13(d,2H), 6.42–6.70(m,5H). IR: ν 1660, 1590, 1445, 1220 cm⁻¹.

Compound (III):

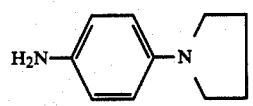

(15) Objective compound: 2-Amino-5-{4-(N,N-di-2-chloroethylamino)phenylaminomethyl}pyrrolo[2,3-d]pyrimidin-4-one.

Yield: 0.426 g

Properties: NMR: δ 3.76(bs,3H), 4.10(d,2H), 6.43–6.70(m,5H). IR: ν 1655, 1595, 1425, 1230 cm⁻¹.

Compound (III):

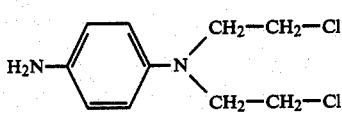

(16) Objective compound: 2-Amino-5-(4-N,N-diallylaminophenylaminomethyl)pyrrolo[2,3-d]pyrimidin-4-one Yield: 0.592 g Properties: NMR: δ 4.10(d,4H), 4.14(d,2H), 5.22(m,4H), 5.90(m,2H), 6.40–6.65(m,5H). IR: ν 1665, 1620, 1590, 1430, 1180 cm⁻¹.

Compound (III):

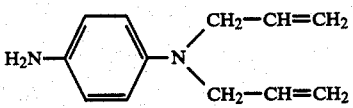

(17) Objective compound: 2-Amino-5-(4-octyloxyphenylaminomethyl)pyrrolo[2,3-d]pyrimidin-4-one.

Yield: 0.785 g

Properties: NMR: δ 0.84(t,3H), 1.10–2.00(bm,12H), 3.98(t,2H), 4.15(d,2H), 6.45–6.80(m,5H). IR: ν 1658, 1620, 1590, 1215 cm⁻¹.

Compound (III):

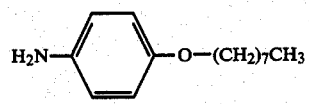

(18) Objective compound: 2-Amino-5-{4-(2-benzoyl-2-methylpropyloxy)phenylaminomethyl}pyrrolo[2,3-d]pyrimidin-4-one.

Yield: 0.762 g

Properties: NMR: δ 1.40(s,6H), 4.00(s,2H), 4.14(d,2H), 6.45–6.80(m,5H), 7.20–7.70(m,5H). IR: ν 1665, 1615, 1595, 1220 cm⁻¹.

Compound (III):

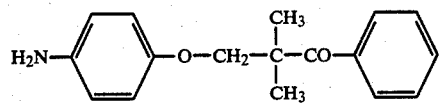

(19) Objective compound: 2-Amino-5-{4-(2-pyridylmethoxy)phenylaminomethyl}pyrrolo[2,3-d]pyrimidin-4-one.

Yield: 0.627 g

Properties: NMR: δ 4.12(d,2H), 4.90(s,2H), 6.40–6.90(m,5H), 7.03–7.30(m,1H), 7.57–7.77(m,1H), 8.63–8.85(m,2H). IR: ν 1660, 1590, 1440, 1235 cm⁻¹.

Compound (III)

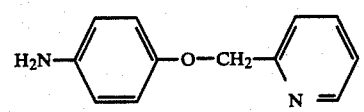

(20) Objective compound: 2-Amino-5-{4-(1-methylcyclohexylmethoxy)phenylaminomethyl}pyrrolo[2,3-d]pyrimidin-4-one.

Yield: 0.624 g

Properties: NMR:δ 1.00(s,3H), 1.40(bs,10H), 3.52(s,2H), 6.45–6.90(m,5H). IR: ν 1658, 1615, 1510, 1220 cm⁻¹.

Compound (III):

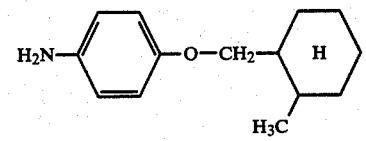

EXAMPLE 3

Production of 2-amino-5-(4-aminophenylaminomethyl)pyrrolo[2,3-d]pyrimidin-4-one

5-N,N-Dibenzylaminomethyl-2-octanoylaminopyrrolo[2,3-d]pyrimidin-4-one (1.95 g) and p-trifluoroacetamidoaniline (4.08 g) are suspended/dissolved in a mixed solution (3:2, 100 ml) of ethanol/tetrahydrofuran, and the reaction is allowed to proceed at 80° C. for 20 hours with stirring. The reaction solution is concentrated to dryness, and the residue is washed with a mixed solution (1:1:40, 200 ml) of methanol/tetrahydrofuran /ethyl ether to give 2-octanoylamino-5-(4-trifluoroacetamidophenylaminomethyl)pyrrolo[2,3-d]pyrimidin-4-one (1.84 g). IR (KBr): 3230, 1940, 1705, 1630, 1540, 1160 cm⁻¹. The compound (1.09 g) is dissolved in a mixed solution (1:1, 100 ml) of methanol/tetrahydrofuran, and after the inside of the reaction system is replaced with nitrogen, concentrated aqueous ammonia (20 ml) is added, followed by stirring at room temperature for 48 hours. The reaction solution is concentrated to dryness under reduced pressure, and the precipitate, which separates out upon addition to the residue of methanol, tetrahydrofuran and ethyl ether, is collected by filtration to give the objective compound (0.536 g).

NMR (DMSO-d₆): δ 4.08(s,2H), 6.43(s,4H), 6.50(s,1H). IR (KBr): ν 1660, 1640, 1590, 1515, 1425, 1250 cm⁻¹.

EXAMPLE 4

Production of
2-amino-5-(4-hydroxyphenylaminomethyl)pyrrolo[2,3-d]pyrimidin-4-one By following a procedure of Example 3, there is obtained 5-(4-benzoyloxyphenylaminomethyl)-2-octanoylaminopyrrolo[2,3-d]pyrimidin-4-one (1.52 g) from 5-N,N-dibenzylaminomethyl-2-octanoylaminopyrrolo[2,3-d]pyrimidin-4-one (1.95 g) and p-benzoyloxyaniline (4.26 g). IR (KBr): $\nu$ 3420, 2960, 1740, 1665, 1510, 1270, 1190, 1060 cm$^{-1}$. The compound (1.02 g) is treated with concentrated aqueous ammonia in methanol/tetrahydrofuran by the procedure of Example 3 to give the objective compound (0.486 g).

NMR (DMSO-d$_6$): $\delta$ 4.16(s,2H), 6.50(bs,1H), 6.54(bs,4H). IR (KBr): $\nu$ 1655, 1610, 1595, 1220 cm$^{-1}$.

EXAMPLE 5

Production of
2-amino-5-(3-ethoxycarbonyl-4-hydroxyphenylaminomethyl)pyrrolo[2,3-d]pyrimidin-4-one By following a procedure similar to that of Example 3, there is obtained 5-(4-benzoyloxy-3-ethoxycarbonylphenylaminomethyl)-2-octanoylaminopyrrolo[2,3-d]pyrimidin-4-one (1.34 g) from 5-N,N-dibenzylaminomethyl-2-octanoylaminopyrrolo[2,3-d]pyrimidin-4-one (1.95 g) and 4-benzoyloxy-3-ethoxycarbonylaniline (5.70 g). IR (KBr): $\nu$ 1740, 1725, 1645, 1610, 1500, 1270 cm$^{-1}$. The compound (1.0 g) is treated with concentrated aqueous ammonia in methanol/tetrahydrofuran by the procedure of Example 3 to give the objective compound (0.712 g).

NMR (DMSO-d$_6$): $\delta$ 0.98(t,3H), 4.06(q,2H), 4.18(d,2H), 6.52 (s,1H), 6.70–7.10(m,2H), 7.28(sd,1H), 7.40–7.85(m,2H), 8.12 (d,2H). IR (KBr): $\nu$ 1740, 1665, 1595, 1430 cm$^{-1}$.

EXAMPLE 6

Production of
2-amino-5-(3-carboxy-4-hydroxyphenylaminomethyl)pyrrolo[2,3-d]pyrimidin-4-one 2-Amino-5-(4-benzoyloxy-3-ethoxycarbonylphenylaminomethyl)-2-octanoylaminopyrrolo[2,3-d]pyrimidin-4-one (1.15 g) as obtained in Example 5 is dissolved in a mixed solution (1:1, 100 ml) of methanol/tetrahydrofuran, and after the inside of the reaction system is replaced with a nitrogen stream, sodium methoxide (0.54 g) is added to the solution, followed by allowing the mixture to stand at room temperature for 24 hours with stirring. Acetic acid is added to the reaction system to conduct neutralization, and the solvent is distilled off under reduced pressure. The residue is washed with methanol, tetrahydrofuran and ethyl ether to give the objective compound (0.681 g).

NMR (DMSO-d$_6$): $\delta$ 4.18(d,2H), 6.53(s,1H), 6.65–7.10(m,2H), 7.26(s,1H). IR (KBr): $\nu$ 1670, 1645, 1605, 1430 cm$^{-1}$.

EXAMPLE 7

Production of 2-amino 5 (2-amino-4-methoxyphenylaminomethyl)pyrrolo[2,3-d]pyrimidin - 4-one 2-Amino-5-(4-methoxy-2-nitropehnylaminomethyl)-pyrrolo[2,3-d]pyrmidin-4-one (301 mg) as obtained in Example 2 (8) is dissolved in a mixed solution (1:1, 410 ml) of methanol/tetrahydrofuran, and 10% palladium-carbon (600 mg of 50% wet product, produced by Engelhardt Co.) is added to the solution to carry out catalytic reduction under a stream of hydrogen. After completion of the reduction, the palladium-carbon is filtered out, and the filtrate is concentrated under reduced pressure. The precipitate, which separates out upon addition to the residue of tetrahydrofuran and ethyl ether, is collected by filtration to give the objective compound (230 mg).

NMR (DMSO-d$_6$): $\delta$ 3.54(s,3H), 4.07(d,2H), 6.12–6.52(m,3H), 6.53(s,1H). IR (KBr): $\nu$ 1657, 1590, 1240 cm$^{-1}$.

EXAMPLE 8

Production of
2-amino-5-(4-hydroxyphenylaminomethyl)pyrrolo[2,3-d]pyrimidin-4-one By the procedure of Example 7, 2-amino-5-{4-(4-chlorobenzyloxy)phenylaminomethyl}pyrrolo[2,3-d]pyrimidin-4-one (100 mg) as obtained in Example 2 (13) is subjected to catalytic reduction by the procedure of Example 7 to give the objective compound (62 mg). Their physico-chemical data were found to agree with those of the compound as obtained in Example 4.

EXAMPLE 9

Production of
2-amino-5-(2-decylthiophenylaminomethyl)pyrrolo[2,3-d]pyrmidin-4-one 2-Amino-5-(2-mercaptophenylaminomethyl)pyrrolo[2,3-d]pyrimidin-4-one (287 mg) as obtained in Example 2 (5), decyl iodide (295 mg) and sodium hydrogen carbonate (330 mg) are suspended/dissolved in 20% aqeuous ethanol (10 ml), and the reaction is allowed to proceed at room temperature for 24 hours with stirring. After completion of the reaction, the solvent is distilled off under reduced pressure, and the residue is separated and purified by silica gel column chromatography to give the objective compound (386 mg).

NMR (DMSO-d$_6$): $\delta$ 0.90(t,3H), 1.10–2.00(bm,16H), 3.95(t.3H), 4.24(d,2H), 6.40–7.28(m,5H). IR (KBr): $\nu$ 1660, 1595, 1460, 1300, 1220 cm$^{-1}$.

EXAMPLE 10

Production of
2-amino-5-(4-propylaminophenylaminomethyl)pyrrolo[2,3-d]pyrimidin-4-one 2-Amino-5-(4-aminophenylaminomethyl)pyrrolo[2,3-d]pyrimidin-4-one (270 mg) as obtained in Example 3 and propyl aldehyde (87 mg) are dissolved in 80% aqueous methanol (10 ml), and sodium cyanoborohydride (126 mg) is added to the solution at room temperature with stirring. After the reaction mixture is made weakly acid with acetic acid, the reaction is allowed to proceed for 15 hours. The reaction solution is concentrated to dryness under reduced pressure, and the residue is purified with use of methanol, tetrahydrofuran and ether to give the objective compound (182 mg).

NMR (DMSO-d$_6$): $\delta$ 0.90(t,3H), 1.67(m,2H), 3.00(t,2H), 4.20 (s,2H), 6.48(bs,4H), 6.50(s,1H). IR (KBr): $\nu$ 1665, 1605, 1595, 1440, 1240 cm$^{-1}$.

What we claim is:

1. A compound of the formula:

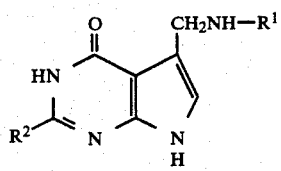

wherein R¹ is (A) a phenyl which has, at the ortho position and/or para position as a substituent or substituents, at least one group represented by the formula: —O—R³, —S—R⁴ or

wherein R³, R⁴, R⁵ and R⁶ are the same or different and each is hydrogen or an $C_{1-24}$ alkyl or phenyl group or wherein R⁵ and R⁶, together with the adjacent nitrogen atom, may form a cyclic amino group of the class consisting of pyrrolidinyl, pyrrolinyl, pyrrolyl, imidazolidinyl, imidazolyl, pyrazolidinyl, pyrazolinyl, pyrazolyl, morpholino, dihydropyridyl, piperidino, N-methylpiperazinyl and N-ethylpiperazinyl, which alkyl, phenyl and cyclic amino group may optionally be mono-, di-or tri-substituted with $C_{1-4}$ alkyl, $C_{2-4}$ alkenyl, $C_{3-6}$ cycloalkyl, $C_{5-6}$ cycloalkenyl, $C_{7-8}$ aralkyl, phenyl, $C_{1-4}$ alkoxy, phenoxy, $C_{1-4}$ alkanoyl, benzoyl, $C_{1-4}$ alkanoyloxy, benzoyloxy, carboxy, $C_{2-4}$ alkoxycarbonyl, carbamoyl, carbamoyl N-monosubstituted by $C_{1-4}$ alkyl, carbamoyl N,N-disubstituted by $C_{1-4}$ alkyl, 1-pyrrolidinylcarbonyl, 1-piperidinylcarbonyl, N-methyl-piperazinylcarbonyl, morpholinocarbonyl, halogen, hydroxy, epoxy, nitro, cyano, trifluoromethyl, diazo, amidino, imino, amino, amino mono-substituted by $C_{1-4}$ alkyl, amino disubstituted by $C_{1-4}$ alkyl, pyrrolidinyl, pyrrolinyl, pyrrolyl, imidazolyl, pyrazolyl, imidazolidinyl, piperidino, morpholino, dihydropyridyl, pyridyl, N-methylpiperazinyl, N-ethylpiperazinyl, $C_{1-4}$ alkanoylamido, benzamido, mercapto, sulfo, sulfino, phosphono, dihydroxyboryl, sulfamoyl, sulfamoyl N-monosubstituted by $C_{1-4}$ alkyl, sulfamoyl N,N-disubstituted by $C_{1-4}$ alkyl, 1-pyrrolidinylsulfonyl, 1-piperidinylsulfonyl, N-methyl-1-piperadinylsulfonyl, morpholinosulfonyl, $C_{1-4}$ alkylthio, phenylthio, $C_{1-4}$ alkylsulfinyl, phenylsulfinyl; $C_{1-4}$ alkylsulfonyl and phenylsulfonyl, which substituent(s) may further be mono- or disubstituted with $C_{1-4}$ alkyl, methoxy, ethoxy, halogen, hydroxy, carboxy, sulfo, phosphono, amidino, amino, methylamino, ethylamino, dimethylamino, diethylamino, morpholino, piperidyl, N-methylpiperazinyl, pyridyl, trimethylammonium, triethylammonium and pyridinium, or wherein R³, R⁴, R⁵ and R⁶ each may represent a protective group of the class consisting of formyl, acetyl, monochloroacetyl, dichloroacetyl, trichloroacetyl, trifluoroacetyl, benzoyl, o-nitrophenoxyacetyl, p-anisoyl, succinoyl, phthaloyl, methoxycarbonyl, ethoxycarbonyl, 2,2,2-trichloroethoxycarbonyl, β-methylsulfonylethoxycarbonyl, t-butoxycarbonyl, benzyloxycarbonyl, p-methoxybenzyloxycarbonyl, β-(p-toluenesulfonyl)ethoxycarbonyl, phenoxycarbonyl, p-methoxyphenoxycarbonyl, thiophenoxycarbonyl, benzyl, p-methoxybenzyl, p-chlorobenzyl, p-nitrobenzyl, trimethylsilyl, t-butyldimethylsilyl, trityl, dimethoxytrityl, methoxymethyl, isopropyloxymethyl, tetrahydrofuranyl, tetrahydropyranyl, methylthiomethyl, benzylthiomethyl, methylthio, ethylthio, phenylthio, aminophenylthio, methoxyphenylthio, nitrophenylthio, $C_{1-4}$-alkyl, vinyl allyl, phenyl p-methoxyphenyl, p-chlorophenyl, 3,4-dimethoxyphenyl, 3,3,4,5-trimethoxyphenyl, phenacyl group, carbamoyl, N-methylcarbamoyl, N-ethylcarbamoyl, N-propylcarbamoyl, N-butylcarbamoyl, N-phenylcarbamoyl, N,N-dimethylcarbamoyl, N,N-diethylcarbamoyl, N,N-dipropylcarbamoyl, N,N-dibutylcarbamoyl, 1-pyrrolidinylcarbamoyl, 1-piperidinylcarbonyl, N-methylpiperazinylcarbamoyl, morpholinocarbamoyl, sulfo, methanesulfonyl, ethanesulfonyl, benzenesulfonyl, p-toluenesulfonyl, or wherein R¹ is (B) a phenyl which is substituted (at any position other than said ortho or para positions at which a group of the formula —OR³, —SR⁴ or —NR⁵R⁶ has been introduced) by one, two or three additional substituents of the class consisting of the formula —O—R³, —S—R⁴ or

introduced, of $C_{1-12}$ alkyl, $C_{2-12}$ alkenyl, $C_{3-12}$ cycloalkyl, $C_{3-8}$ cycloalkenyl, $C_{7-13}$ aralkyl, $C_{6-10}$ aryl, $C_{1-4}$ alkoxy, phenoxy, $C_{1-4}$ alkanoyl, benzoyl, $C_{1-4}$ alkanoyloxy, benzoyloxy carboxy, $C_{2-4}$ alkoxycarbonyl, carbamoyl, carbamoyl N-monosubstituted by $C_{1-4}$alkyl, carbamoyl N,N-disubstituted by $C_{1-4}$ alkyl, 1-pyrrolidinylcarbamoyl, 1-piperidinylcarbamoyl, N-methylpiperazinylcarbamoyl, morpholinocarbamoyl, halogen, hydroxy, epoxy, nitro, cyano, trifluoromethyl, diazo, amidino, imino, amino, amino mono-substituted by $C_{1-4}$ alkyl, amino disubstituted by $C_{1-4}$ alkyl, pyrrolidinyl, pyrrolinyl, pyrrolyl, imidazolyl, pyrazolyl, imidazolidinyl, piperidino, morpholino, dihydropyridyl, pyridyl, N-methylpiperazinyl, N-ethylpiperazinyl, $C_{1-4}$ alkanoylamido, benzamido, mercapto, sulfo, sulfino, phosphono, dihydroxyboryl, sulfamoyl, sulfamoyl N-monosubstituted by $C_{1-4}$ alkyl, sulfamoyl N,N-disubstituted by $C_{1-4}$ alkyl, 1-pyrrolidinylsulfonyl, 1-piperidinylsulfonyl, N-methyl-1-piperazinylsulfonyl, morpholinosulfonyl, $C_{1-10}$ alkylthio, phenylthio, $C_{1-10}$ alkylsulfinyl, phenylsulfinyl, $C_{1-8}$ alkylsulfonyl and phenylsulfonyl, which group(s) may further be mono-or di-substituted with $C_{1-4}$ alkyl, methoxy, ethoxy, halogen, hydroxy, carboxy, sulfo, phosphono, amidino, amino, methylamino, ethylamino, dimethylamino, diethylamino, morpholino, piperidyl, N-methylpiperazinyl, pyridyl, trimethylammonium, triethylammonium and pyridinium; R² is an amino group which may be protected, the protective group in the amino group being $C_{1-18}$ alkanoyl, mono-, di-or trichloroacetyl, trifluoroacetyl, 2-ethylhexanoyl, benzoyl, o-anisoyl, o-cyanobenzoyl, o-nitrobenzoyl, toluoyl, phthaloyl, naphthoyl, $C_{1-15}$ alkoxycarbonyl, 2,2,2-trichloroethoxycarbonyl, β-methoxysulfonylethoxycarbonyl, benzyloxycarbonyl, p-methoxybenzyloxycarbonyl, 2-(p-xenyl)isopropoxycarbonyl, β-(p-toluenesulfonyl)ethoxycarbonyl, $C_{6-12}$ aryloxycarbonyl, p-methoxyphenoxycarbonyl, $C_{1-7}$ thioalkoxycarbonyl, thiobenzyloxycarbonyl, thioaryloxycarbonyl, benzyl, p-methoxybenzyl, 3,4,5-trimethoxybenzyl, di(p-methoxybenzyl)-methyl, trityl, monomethoxytrityl, dimethylaminomethylene, diethylaminomethylene, dipropylaminomethylene, diphenylaminomethylene, p-nitrobenzylphosphoryl, p-bromobenzylphosphoryl, dibenzylphosphoryl, di(p-nitrobenzyl)phosphoryl, di(o-bromobenzyl)phosphoryl, di(p-iodobenzyl)phosphoryl, hydroxy sulfonyl, benzylsulfonyl, phenacylsulfonyl, benzenesulfonyl, toluenesulfonyl, trimethylsilyl, or tert-butyldimethylsilyl, or pharmaceutically acceptable salt thereof.

2. A compound as claimed in claim 1, wherein $R^1$ is phenyl which has, at the ortho position and/or para position as a substituent, at least one group represented by the formula: $-O-R^3$, $-S-R^4$,

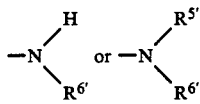

wherein $R^{3'}$ is $C_{5-24}$ alkyl, $C_{1-24}$ alkyl which is substituted or phenyl which may be substituted, $R^4$ is hydrogen or an alkyl or phenyl group which may be substituted, $R^{5'}$ and $R^{6'}$ are the same or different and each is $C_{5-24}$ alkyl, $C_{1-24}$ alkyl which is substituted or phenyl which may be substituted, $R^{5'}$ and $R^{6'}$ may form, together with the adjacent nitrogen atom, a cyclic amino group which may be substituted, the substituent of said $C_{1-24}$ alkyl, phenyl and cyclic amino is of the class consisting of $C_{1-4}$ alkyl, $C_{2-4}$ alkenyl, $C_{3-6}$ cycloalkyl, $C_{5-6}$ cycloalkenyl, $C_{7-8}$ aralkyl, phenyl, $C_{1-4}$ alkoxy, phenoxy, $C_{1-4}$ alkanoyl, benzoyl, $C_{1-4}$ alkanoyloxy, benzyloxy, carboxy, $C_{2-4}$ alkoxycarbonyl, carbamoyl, carbamoyl N-monosubstituted by $C_{1-4}$ alkyl, carbamoyl N,N-disubstituted by $C_{1-4}$ alkyl, 1-pyrrolidinylcarbamoyl, 1-piperidinylcarbamoyl, N-methylpiperazinylcarbamoyl, morpholinocarbamoyl, halogen, hydroxy, epoxy, nitro, cyano, trifluoromethyl, diazo, amidino, imino, amino, amino mono-substituted by $C_{1-4}$ alkyl, amino disubstituted by $C_{1-4}$ alkyl, pyrrolidinyl, pyrrolinyl, pyrrolyl, imidazolyl, pyrazolyl, imidazolidinyl, piperidino, morpholino, dihydropyridyl, pyridyl, N-methylpiperazinyl, N-ethylpiperazinyl, $C_{1-4}$ alkanoylamido, benzamido, mercapto, sulfo, sulfino, phosphono, dihydroxyboryl, sulfamoyl, sulfamoyl N-monosubstituted by $C_{1-4}$ alkyl, sulfamoyl N,N-disubstituted by $C_{1-4}$ alkyl, 1-pyrrolidinylsulfonyl, 1-piperidinylsulfonyl, N-methyl-1-piperazinylsulfonyl, morpholinosulfonyl, $C_{1-4}$ alkylthio, phenylthio, $C_{1-4}$ alkylsulfinyl, phenylsulfinyl $C_{1-4}$ alkylsulfonyl and phenylsulfonyl, said substituent(s) may further be mono- or di-substituted with $C_{1-4}$ alkyl, methoxy, ethoxy, halogen, hydroxy, carboxy, sulfo, phosphono, amidino, amino, methylamino, ethylamino, dimethylamino, diethylamino, morpholino, piperidyl, N-methylpiperazinyl, pyridyl, trimethylammonium, triethylammonium and pyridinium, or wherein $R^3$, $R^4$, $R^5$ and $R^6$ each may represent a protective group of the class consisting of formyl, acetyl, monochloroacetyl, dichloroacetyl, trichloroacetyl, trifluoroacetyl, benzoyl, o-nitrophenoxyacetyl, p-anisoyl, succinoyl, phthaloyl, methoxycarbonyl, ethoxycarbonyl, 2,2,2-trichloroethoxycarbonyl, β-methylsulfonylethoxycarbonyl, t-butoxycarbonyl, benzyloxycarbonyl, p-methoxybenzyloxycarbonyl, β-(p-toluenesulfonyl)ethoxycarbonyl, phenoxycarbonyl, p-methoxyphenoxycarbonyl, thiophenoxycarbonyl, benzyl, p-methoxybenzyl, p-chlorobenzyl, p-nitrobenzyl, trimethylsilyl, t-butyldimethylsilyl, trityl, dimethoxytrityl, methoxymethyl, isopropyloxymethyl, tetrahydrofuranyl, tetrahydropyranyl, methylthiomethyl, benzylthiomethyl, methylthio, ethylthio, phenylthio, aminophenylthio, methoxyphenylthio, nitrophenylthio, methyl, ethyl, isopropyl, t-butyl, vinyl, allyl phenyl, p-methoxyphenyl, p-chlorophenyl, 3,4-dimethoxyphenyl, 3,4,5-trimethoxyphenyl, phenacyl, carbamoyl, N-methylcarbamoyl, N-ethylcarbamoyl, N-propylcarbamoyl, N-butylcarbamoyl, N-phenylcarbamoyl, N,N-dimethylcarbamoyl, N,N-diethylcarbamoyl, N,N-dipropylcarbamoyl, N,N-dibutylcarbamoyl, 1-pyrrolidinylcarbonyl, 1-piperidinylcarbonyl N-methyl-piperazinylcarbonyl, morpholinocarbonyl, sulfo methanesulfonyl, ethanesulfonyl, benzenesulfonyl, p-toluenesulfonyl.

3. A compound as claimed in claim 1, wherein $R^1$ is phenyl which has, at the ortho position and/or para position as a substituent or substituents, at least one group of hydroxy, methoxy, ethoxy, propyloxy, butyloxy, octyloxy, phenoxy, benzyloxy, mercapto, methylthio, ethylthio, propylthio, butylthio, decylthio, phenylthio, amino, methylamino, ethylamino, propylamino, butylamino, dimethylamino, diethylamino, dipropylamino, dibutylamino, phenylamino, formyloxy, acetyloxy, propionyloxy, butyloxy, benzoyloxy, formamido, acetamido, trifluoroacetamido, benzamido, pyrrolidinyl, pyrrolyl, imidazolyl, morpholino, piperidino, N-methylpiperazinyl or N-ethylpiperazinyl.

4. A compound as claimed in claim 1, wherein $R^1$ is phenyl which has, at the ortho position and/or para position as a substituent or substituents, at least one group of octyloxy, phenoxy, benzyloxy, mercapto, methylthio, ethylthio, propylthio, butylthio, decylthio, ·phenylthio, phenylamino, formyloxy, acetyloxy, propionyloxy, butyryloxy, benzoyloxy, formamido, acetamido, trifluoroacetamido, benzamido, pyrrolidinyl, pyrrolyl, imidazolyl, morpholino, piperidino, N-methylpiperazinyl or N-ethylpiperazinyl.

5. A compound as claimed in claim 1, wherein the group, which the phenyl represented by $R^1$ may have at any position other than the ortho position and/or para position having the group of the formula $-O-R^3$, $-S-R^4$ or

is methyl, ethyl, propyl, butyl, vinyl, allyl, cyclopentyl, cyclohexyl, benzyl, phenyl, hydroxy, methoxy, ethoxy, propoxy, butoxy, phenoxy, formyl, acetyl, benzoyl, acetyloxy, carboxy, methoxycarbonyl, ethoxycarbonyl, propoxycarbonyl, carbamoyl, halogen, nitro, cyano, trifluoromethyl, amino, methylamino, ethylamino, propylamino, isopropylamino, butylamino, dimethylamino, diethylamino, dipropylamino, diisopropylamino, dibutylamino, pyrrolidinyl, morpholino, piperidino, N-methylpiperazinyl, N-ethylpiperazinyl, sulfo, phosphono, sulfamoyl, N-methylsulfamoyl, N-ethylsulfamoyl, N-propylsulfamoyl, N-isopropylsulfamoyl, N-butylsulfamoyl, N,N-dimethylsulfamoyl, N,N-diethylsulfamoyl, N,N-dipropylsulfamoyl, N,N-dibutylsulfamoyl, methylthio, ethylthio, propylthio, butylthio, phenylthio, methylsulfonyl, ethylsulfonyl or phenylsulfonyl.

6. A compound as claimed in claim 1, wherein the protective group in the amino group which may be protected as represented by $R^2$ is formyl, acetyl, monochloroacetyl, trifluoroacetyl, octanoyl, 2-ethylhexanoyl, benzoyl, p-anisoyl, phthaloyl, methoxycarbonyl, ethoxycarbonyl, 2,2,2-trichloroethoxycarbonyl, tert-butoxycarbonyl, benzyloxycarbonyl, β-methylsulfonylethoxycarbonyl, phenoxycarbonyl or dimethylaminomethylene.

7. A compound as claimed in claim 1, wherein the compound is one in which $R^1$ is 3,4,5-trimethoxyphenyl and $R^2$ is amino.

8. A compound as claimed in claim 1, wherein the compound is one in which $R^1$ is 2-mercaptophenyl and $R^2$ is amino.

9. A compound as claimed in claim 1, wherein the compound is one in which $R^1$ is 4-N,N-di-2-chloroethylamino)phenyl and $R^2$ is amino.

10. A compound as claimed in claim 1, wherein the compound is one in which $R^1$ is 4-octyloxyphenyl and $R^2$ is amino.

11. A compound as claimed in claim 1, wherein the compound is one in which $R^1$ is 4-aminophenyl and $R^2$ is amino.

* * * * *